(12) United States Patent
Klegraf et al.

(10) Patent No.: US 12,043,593 B2
(45) Date of Patent: Jul. 23, 2024

(54) METHOD FOR PREPARATION OF POTASSIUM 5-IODO-2-CARBOXYBENZENE SULFONATE

(71) Applicant: ARXADA AG, Visp (CH)

(72) Inventors: Ellen Klegraf, Naters (CH); Patrick Schanen, Sierre (CH); Florencio Zaragoza Doerwald, Buochs (CH)

(73) Assignee: ARXADA AG, Visp (CH)

( * ) Notice: Subject to any disclaimer, the term of this patent is extended or adjusted under 35 U.S.C. 154(b) by 670 days.

(21) Appl. No.: 17/265,740

(22) PCT Filed: Sep. 24, 2019

(86) PCT No.: PCT/EP2019/075740
§ 371 (c)(1),
(2) Date: Feb. 3, 2021

(87) PCT Pub. No.: WO2020/064753
PCT Pub. Date: Apr. 2, 2020

(65) Prior Publication Data
US 2021/0261501 A1  Aug. 26, 2021

(30) Foreign Application Priority Data

Sep. 25, 2018 (EP) .................................. 18196688
Sep. 27, 2018 (EP) .................................. 18197049

(51) Int. Cl.
*C07C 303/32* (2006.01)
*B01J 21/18* (2006.01)
*B01J 23/44* (2006.01)

(52) U.S. Cl.
CPC ............. *C07C 303/32* (2013.01); *B01J 21/18* (2013.01); *B01J 23/44* (2013.01)

(58) Field of Classification Search
CPC .......... C07C 303/32; B01J 21/18; B01J 23/44
See application file for complete search history.

(56) References Cited

U.S. PATENT DOCUMENTS

| 5,550,237 A | 8/1996 | Jan |
| 5,618,975 A * | 4/1997 | Wagner ................... C07B 37/04 564/99 |
| 6,147,248 A | 11/2000 | Willms et al. |
| 7,642,374 B2 | 1/2010 | Yoshimura et al. |
| 2017/0315059 A1 * | 11/2017 | Miller .................... C09K 11/06 |

FOREIGN PATENT DOCUMENTS

| CN | 101497565 | 8/2009 |
| CN | 101838179 | 9/2010 |
| CN | 101845233 | 9/2010 |
| CN | 106187741 | 12/2016 |
| WO | WO-2012159116 A2 * | 11/2012 ............. C09K 11/06 |

OTHER PUBLICATIONS

International Search Report and Written Opinion for PCT/EP2019/075740 dated Dec. 6, 2019, 7 pages.

* cited by examiner

*Primary Examiner* — Yate' K Cutliff
(74) *Attorney, Agent, or Firm* — Dority & Manning, P.A.

(57) ABSTRACT

The invention discloses a method for the preparation of potassium 5-iodo-2-carboxybenzene sulfonate by diazotization of 5-amino-2-carboxybenzene sulfonate and subsequent reaction with KI.

13 Claims, No Drawings

METHOD FOR PREPARATION OF POTASSIUM 5-IODO-2-CARBOXYBENZENE SULFONATE

CROSS REFERENCE TO RELATED APPLICATIONS

This application is the U.S. National Stage entry of International Application Number PCT/EP2019/075740 filed under the Patent Cooperation Treaty having a filing date of Sep. 24, 2019, which claims priority to European Patent Application No. 18196688.8 having a filing date of Sep. 25, 2018, and European Patent Application No. 18197049.2 having a filing date of Sep. 27, 2018, which are incorporated herein by reference.

The invention discloses a method for the preparation of potassium 5-iodo-2-carboxybenzene sulfonate by diazotization of 5-amino-2-carboxybenzene sulfonate and subsequent reaction with KI.

BACKGROUND OF THE INVENTION

U.S. Pat. No. 5,550,237 A discloses compounds (I) $HO_3S$—Ar—CO-Nuc in which Ar is (substituted) arylene and Nuc is the radical of a nucleophile Nuc-H and which are valuable intermediates for pharmaceuticals, crop protection products and colorants, they can be prepared by reacting an diazonium salt of the formula (II) —$O_3S$—Ar—$N_2$+ with CO in the presence of a metal catalyst of group VIII of the Periodic System or Cu and Nuc-H or a salt thereof.

Example 1 discloses the preparation of monosodium 5-iodocarboxybenzenesulfonate. The diazonium salt is isolated and then is carbonylated in the solvent acetonitrile with the help of homogeneous catalysis in form of palladium diacetate.

There was a need for a method for preparation of 5-iodo-2-carboxybenzenesulfonate, which does not need an isolation of a diazonium salt, sinces isolated diazonium salts always pose a risk of decomposition. The method should not require mandatorily the use of acetonitrile, preferably of no organic solvent in larger amounts, also not the use of a homogenous palladium catalyst, as they are usually difficult to recycle, also not of CO which is toxic and poses therefore a risk.

WO 2012159116 relates to fluorescent probes for monitoring voltage by photoinduced electron transfer. It discloses, inter alia, a method for preparation of 4-iodo-2-sulfobenzoic acid via the reduction of 4-nitro-2-sulfobenzoic acid with iron, and isolation of the resulting 4-amino-2-sulfobenzoic acid in the form of its HCl salt. After formation of the 4-amino-2-sulfobenzoic acid sodium salt, reaction with sodium nitrite and sodium iodide provides 4-iodo-2-sulfobenzoic acid sodium salt. The latter is a sticky salt, which is tedious to filtrate and isolate. Hence, this process is not suitable for large-scale production as it produces a lot of iron waste and does not produce high yields.

A method for preparation of 5-iodo-2-carboxybenzenesulfonate, was found which does not need an isolation of a diazonium salt, does not require mandatorily the use of acetonitrile, if an organic solvent is used at all then only in smaller amounts, the method does not the use a homogenous palladium catalyst and also not CO. The 4-iodo-2-sulfobenzoic acid potassium salt is easy to isolate without requiring further recrystallization steps. The method of the invention provides high yields while being much cleaner than the prior art procedures.

Abbreviations:
% percent are percent by weight (wt %), if not stated otherwise
eq equivalent

SUMMARY OF THE INVENTION

Subject of the invention is a method for the preparation of compound of formula (3),

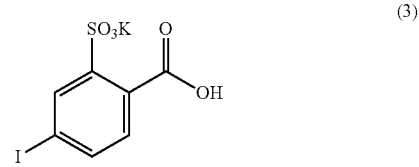

the method comprises two steps STEP1 and STEP2, in STEP1 compound of formula (2)

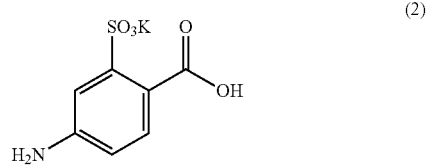

is reacted in a reaction REAC1 with $KNO_2$ in the presence of HCl providing the diazonium salt of compound of formula (2);
in STEP2 the diazonium salt of compound of formula (2) is reacted in a reaction REAC2 with KI providing compound of formula (3).

DETAILED DESCRIPTION OF THE INVENTION

Preferably, REAC1 is done in aqueous medium;
preferably, the weight of the water is from 4 to 20 fold, more preferably from 5 to 15 fold, even more preferably from 5 to 10 fold, of the weight of compound of formula (2).

Preferably, compound of formula (2) is used in form of a mixture with water for REAC1.

Preferably, no acetonitrile is used in REAC1, more preferably, no organic solvent is used as solvent for REAC1.

Preferably, REAC1 is done in the presence of HCl.

Preferably, the HCl is used for REAC1 in form of an aqueous solution, more preferably in form of an aqueous solution with a content of from 25 to 35 wt %, even more preferably of from 30 to 35 wt % of HCl.

Preferably, the molar amount of HCl in REAC1 is from 2 to 10 eq, more preferably from 2 to 7.5 eq, even more preferably from 2 to 5 eq, especially from 2 to 4 eq, of the molar amount of compound of formula (2).

Preferably, $KNO_2$ is used for REAC1 in form of an aqueous solution, more preferably in form of mixture with water with a content of from 30 to 65 wt %, even more preferably of from 35 to 65 wt % of $KNO_2$, the wt % being based on the weight if the mixture of $KNO_2$ with water.

Preferably, the molar amount of $KNO_2$ in REAC1 is from 1 to 2 eq, more preferably from 1 to 1.8 eq, even more preferably from 1 to 1.7 eq, of the molar amount of compound of formula (2).

Preferably, compound of formula (2), preferably in form of a mixture with water, is first mixed with HCl, the HCl is preferably used in form of an aqueous solution, then this mixture of compound of formula (2) and HCl is mixed with $KNO_2$, the $KNO_2$ is preferably used in form of an aqueous solution.

Preferably, the mixing of compound of formula (2) with HCl is done at a temperature from 30 to 80° C., more preferably from 40 to 70° C., even more preferably of from 50 to 70° C.

Preferably, the time for the mixing of compound of formula (2) and HCl is from 30 min to 4 h, more preferably of from 45 min to 3 h, even more preferably of from 45 min to 2 h, especially of from 45 min to 1.5 h.

Preferably, the mixing of compound of formula (2) and HCl is done at atmospheric pressure.

Preferably, REAC1 is done at a temperature TEMP1, TEMP1 is from −10 to 20° C., more preferably from −5 to 10° C., even more preferably of from −5 to 5° C.

Preferably, the reaction time TIME1 of REAC1 is from 30 min to 6 h, more preferably of from 45 min 4 h, even more preferably of from 1 to 2 h.

Preferably, REAC1 is done at atmospheric pressure.

Preferably, KI is used for REAC2 in form of an aqueous solution, more preferably in form of an mixture with water with a content of from 30 to 60 wt %, even more preferably of from 35 to 55 wt % of KI, the wt % being based on the weight if the mixture of KI with water.

Preferably, the molar amount of KI in REAC2 is from 1 to 2 eq, more preferably from 1 to 1.8 eq, even more preferably from 1 to 1.7 eq, of the molar amount of compound of formula (2).

Preferably, REAC2 is done at a temperature TEMP2, TEMP2 is from −10 to 70° C., more preferably from −5 to 60° C., even more preferably of from 0 to 60° C.

Preferably, the reaction time TIME2 of REAC2 is from 2 to 10 h, more preferably of from 2 to 8 h, even more preferably of from 2 to 6 h, especially from 3 to 5 h.

Preferably, REAC2 is done at atmospheric pressure.

TIME2 comprises a time TIMEMIX2 for mixing of the reaction mixture obtained from REAC1 with KI and a time TIMESTIRR2 for stirring after said mixing.

Preferably, TIMEMIX2 is from 15 min to 2 h, more preferably from 20 min to 1 h, even more preferably from 30 min to 1 h.

Preferably, TIMESTIRR2 is up to 9 h 45 min, more preferably up to 7 h 45 min, even more preferably up to 5 h 45 min, especially up to 4 h 45 min.

Preferably, TIMEMIX2 and TIMESTIRR2 add up to TIME2.

Preferably, the mixing during TIMEMIX2 is done at a temperature TEMPMIX2, preferably TEMPMIX2 is from −10 to 40° C., more preferably from −5 to 30° C., even more preferably of from 0 to 30° C.

Preferably, the stirring during TIMESTIRR2 is done at a temperature TEMPSTIRR2, preferably TEMPSTIRR2 is from 0 to 70° C., more preferably from 0 to 60° C.

Preferably, the stirring during TIMESTIRR2 is done with an increase of TEMPSTIRR2 during TIMESTIRR2, starting from lower temperature and going to higher temperature; said lower temperature being from −10 to below 15° C., preferably from −5 to below 15° C.; said higher temperature being from 15 to 70° C., more preferably from 20 to 70° C., even more preferably of 20 to 60° C.

Preferably at least 60%, preferably at least 70%, even more preferably at least 75%, of the stirring during TIMESTIRR2 is done at said higher temperature.

When the stirring during TIMESTIRR2 is done with said increase of TEMPSTIRR2 during TIMESTIRR2, starting from said lower temperature and going to said higher temperature, then preferably the mixing during TIMEMIX2 is done at said lower temperature.

REAC1 or REAC2 or both can be done in the presence of small amounts of xylene, small amounts of xylene are preferably molar amounts of xylene of from 0.01 to 2 eq, more preferably of from 0.05 to 1 eq, even more preferably of from 0.05 to 0.75 eq, especially of from 0.1 to 0.75 eq, more especially of from 0.1 to 0.5 eq, even more especially of from 0.2 to 0.5 eq, of the molar amount of compound of formula (2).

Preferably, if xylene is used, then both REAC1 and REAC are done in the presence of said small amounts of xylene.

After REAC1 excess of $KNO_2$, that is excess of the nitrite anion, can be destroyed. Means for the destruction of $KNO_2$ are known to the skilled person, various substances can be used such as mono-nitroaniline, dinitroaniline, hydroxyl ammoniumchlorid, sulfanilic acid, sulfamic acid, sulfanilamide or urea. These substances are typically mixed with the reaction mixture after REAC1 and cause the destruction of the nitrite anion, that is the $KNO_2$. Preferably the nitrite anion, is destructed by a mixing of the reaction mixture after REAC1 with urea. The urea is preferably used in form of an aqueous solution, more preferably in form of an aqueous solution with 20 wt % of urea. Preferably, urea is charged after REAC1 and before the mixing with KI.

REAC1 and REAC2 can be done under inert atmosphere, preferably $N_2$ is used for inertization.

Preferably, REAC1 and REAC2 are done consecutively without isolation of the diazonium salt of compound of formula (2), more preferably, REAC1 and REAC2 are consecutively and done in one pot.

After REAC2 compound of formula (3) can be isolated by standard methods known to the skilled person, such as filtration, washing and drying.

Preferably, compound of formula (2) is prepared by a reduction of compound of formula (1).

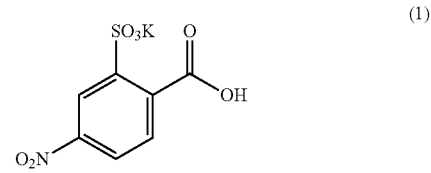
(1)

Preferably, the reduction is done with $H_2$, Fe, Zn, Sn, hydrazine or $NaBH_4$; more preferably, the reduction is done with $H_2$.

Preferably, the reduction is done in the presence of a catalyst CAT, CAT is Pd/C.

Pd/C is a palladium catalyst in charcoal.

Preferably, CAT has a content of Pd of from 1 to 10 wt %, more preferably of from 2 to 7.5 wt %, even more preferably of from 3 to 7.5 wt %, the wt % being based on the total weight of CAT.

Preferably, the amount of CAT used in the reduction is from 0.5 to 5 wt %, more preferably from 0.75 to 4 wt %, even more preferably from 1 to 3 wt %, especially from 1.5 to 3 wt %, the wt % being based on the weight of compound of formula (1).

Preferably, the reduction is done in water as solvent.

When water is used for the reduction then the weight of water is from 3 to 10 fold, more preferably from 4 to 7.5 fold, of the weight of compound of formula (1).

Preferably, $H_2$ is applied for the reduction at a pressure of from 1 to 100 bar, more preferably of from 2.5 to 50 bar, even more preferably of from 5 to 25 bar, especially of from 5 to 15 bar.

Preferably, the reduction is done at a temperature REDTEMP, REDTEMP is from 50 to 100° C., more preferably from 60 to 90° C., even more preferably of from 60 to 80° C.

Preferably, the reaction time REDTIME of the reduction is from 1 to 10 h, more preferably of from 1 to 8 h, even more preferably of from 1 to 6 h, especially from 1 to 4 h.

The reduction can be done in the presence of small amounts of xylene, small amounts of xylene are preferably molar amounts of xylene of from 0.01 to 2 eq, more preferably of from 0.05 to 1 eq, even more preferably of from 0.05 to 0.75 eq, especially of from 0.1 to 0.75 eq, more especially of from 0.1 to 0.5 eq, even more especially of from 0.2 to 0.5 eq, of the molar amount of compound of formula (1).

After the reduction CAT can be separated by standard methods known to the skilled person, such as filtration.

After the reduction compound of formula (2) can be isolated by standard methods known to the skilled person, such as distillation, crystallization, extraction, filtration, washing and drying.

Preferably, the reduction is done in water and compound of formula (2) is obtained from the reduction of an aqueous solution. Preferably, CAT is separated after the reduction by filtration of said aqueous solution. Preferably, said aqueous solution is used as such for REAC1.

Examples

Materials

KNO$_2$: 97%, extra pure, Acros Organics part of Thermo Fisher Scientific, Belgium, No. 453190010

KI: for analysis EMSURE® ISO, Reag. Ph Eur, EMD Millipore of Merck KGaA, Germany, No. 1.05043.2500

Urea: >=99.5%, Sigma-Aldrich of Merck KGaA, Germany, U1250 potassium 5-nitro-2-carboxybenzenesulfonate, CAS 5344-48-9, can be purchased from Fluorochem Ltd., UK Pd/C catalyst: 5 wt % Pd on charcoal, type CE 101 XR/W, Evonik Industries AG, Germany Example 1: Hydrogenation of potassium 5-nitro-2-carboxybenzenesulfonate A mixture of 50.8 g (0.178 mol) of potassium 5-nitro-2-carboxybenzenesulfonate and 264 mL of water was charged into an autoclave. 1.15 g of Pd/C catalyst are added. The autoclave was closed and flushed five times with nitrogen at 5 bars while stirring. The reaction mixture was heated to 70° C. The stirring was stopped and the reactor was flushed 3 times with hydrogen at 8 bars. The reactor was then pressurized with hydrogen at 8 bars and the reaction was started by switching on the stirrer. The stirring was continued for 2 h at 70° C., after that time no more hydrogen was taken up. The reaction mixture was cooled to room temperature and the reactor was flushed three times with nitrogen at 8 bars. Then the Pd/C catalyst was separated from the reaction mixture by filtration. 310 g of an aqueous solution containing 14.7 wt % of potassium 5-amino-2-carboxybenzenesulfonate was obtained.

Yield: 100%

1H NMR (DMSO-d$_6$, 400 MHZ): delta$_H$ 6.66 (1H, dd, J=8.4, 2.4 Hz), 7.16 (1H, d, J=2.4 Hz), 7.71 (1H, d, J=8.8 Hz).

Example 2: Synthesis of potassium 5-iodo-2-carboxybenzenesulfonate

In a reactor and under inert atmosphere (N$_2$), 300 g of an aqueous solution containing 14.7 wt % of potassium 5-amino-2-carboxybenzenesulfonate (14.7 wt %, 173 mmol), prepared according to Example 1, was heated to 60° C. 59.9 g of aqueous HCl 32 wt % (3 eq) were added within 1 h under stirring. The resulting suspension was cooled to 0° C. and 37.5 g of an aqueous solution of KNO$_2$ 40 wt % (1.02 eq) were added within 1 h. The mixture was stirred for 30 min at 0° C., then 73.1 g of a 40 wt % aqueous solution of KI (1.02 eq) were added within 40 min. After the addition of the KI, the mixture was heated to 50° C. within 60 min and stirred at 50° C. for 2 hours. Then the mixture was cooled to 4°C and the product was isolated by filtration providing 51.98 g of wet presscake (82.6 wt % solid content) of the product potassium 5-iodo-2-carboxybenzenesulfonate (67.9% yield).

The mother liquour contained additional 2.9 wt % of product (17.3% yield) giving a total yield of 85.2%.

1H NMR (DMSO-d$_6$, 400 MHZ): delta$_H$ 7.43 (1H, d, J=8.0 Hz), 7.87 (1H, dd, J=8.0, 2.0 Hz), 8.15 (1H, d, J=1.6 Hz).

Example 3: Synthesis of potassium 5-iodo-2-carboxybenzenesulfonate

Example 2 was repeated with the sole difference, that excess KNO$_2$ was destroyed by the addition of 1 g of a 20 wt % aqueous solution of urea (0.02 eq), the urea was added after the stirring of the mixture for 30 min at 0° C. and before the addition of the 73.1 g of a 40 wt % aqueous solution of KI (1.02 eq).

Total yield: 80.8%

Example 4: Synthesis of potassium 5-iodo-2-carboxybenzenesulfonate

Example 2 was repeated with the sole difference, that
the KNO$_2$ was used in form of a 60 wt % aqueous solution (instead of the 40 wt % aqueous solution of Example 2), and
the KI was used on form of a 50 wt % aqueous solution (instead of the 40 wt % aqueous solution of Example 2).

Total yield: 81.7%

Example 5: Synthesis of potassium 5-iodo-2-carboxybenzenesulfonate

Example 4 was repeated with the sole difference, that the 60 wt % aqueous solution of KI was added at a temperature of 25° C. (instead of addition at 0° C. of Example 4).

Total yield 83.1%

Example 6: Synthesis of potassium 5-iodo-2-carboxybenzenesulfonate

Example 3 was repeated with the sole difference, that the heating after the addition of the KI was done stepwise by heating first within 25 min to 25° C. and then stirring for 1 hour at that 25° C., then heating within 25 min to 50° C. and stirring at 50° C. for 2 h (instead of heating to 50° C. within 60 min and stirring at 50° C. for 2 hours of Example 3).

Total yield 81.1%

Example 7: Synthesis of potassium 5-iodo-2-carboxybenzenesulfonate

Example 6 was repeated with the sole difference, that that 1.1 eq of KNO2 and 1.2 eq of KI were added (instead of 1.02 eq of $KNO_2$ and of 1.02 eq of KI of Example 6).
Total yield 88.1%

Example 8: Synthesis of potassium 5-iodo-2-carboxybenzenesulfonate

Example 7 was repeated with the sole difference, that the $KNO_2$ and the KI were added at a temperature of 10° C. (instead of the temperature of 0° C. of Example 7).
Total yield 81.9%

Example 9: Synthesis of potassium 5-iodo-2-carboxybenzenesulfonate

Example 4 was repeated with the sole difference, that 1.5 eq of $KNO_2$ and 1.5 eq of KI were added (instead of the 1.02 eq of $KNO_2$ and the 1.02 eq of KI of Example 4).
Total yield 84.7%

Example 10: Synthesis of potassium 5-iodo-2-carboxybenzenesulfonate

Example 4 was repeated with the sole difference, that 0.3 eq of Xylene were added after the stirring for 30 min at 0° C. and prior to the addition of the KI solution (instead of no additive in Example 4).
Total yield 88.0%

Example 11: Synthesis of potassium 5-iodo-2-carboxybenzenesulfonate

Example 10 was repeated with the sole difference, that 0.1 eq of Xylene were added (instead of 0.3 eq in Example 10).
Total yield 82.9%

The invention claimed is:
1. A method for the preparation of compound of formula (3),

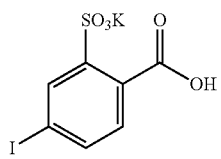
(3)

the method comprises two steps STEP1 and STEP2,
in STEP1 compound of formula (2)

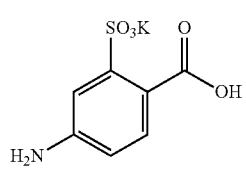
(2)

is reacted in a reaction REAC1 with $KNO_2$ in the presence of HCl providing the diazonium salt of compound of formula (2); and
in STEP2 the diazonium salt of compound of formula (2) is reacted in a reaction REAC2 with KI providing compound of formula (3).

2. The method according to claim 1, wherein REAC1 is done in aqueous medium.

3. The method according to claim 1, wherein the reaction time TIME2 of REAC2 is from 2 to 10 h.

4. The method according to claim 3, wherein TIME2 comprises a time TIMEMIX2 for mixing of the reaction mixture obtained from REAC1 with KI and a time TIMESTIRR2 for stirring after said mixing; TIMEMIX2 is from 15 min to 2 h.

5. The method according to claim 4, wherein
the mixing during TIMEMIX2 is done at a temperature TEMPMIX2,
the stirring during TIMESTIRR2 is done at a temperature TEMPSTIRR2,
the stirring during TIMESTIRR2 is done with an increase of TEMPSTIRR2 during TIMESTIRR2, starting from lower temperature and going to higher temperature,
said lower temperature being from −10 to below 15° C.;
said higher temperature being from 15 to 70° C.; and
the mixing during TIMEMIX2 is done at said lower temperature.

6. The method according to claim 1, wherein
REAC1 and/or REAC2 can be done in the presence of small amounts of xylene, small amounts are molar amounts of xylene of from 0.01 to 2 eq of the molar amount of compound of formula (2).

7. The method according to claim 1, wherein
REAC1 or REAC2 or both are done consecutively without isolation of the diazonium salt of compound of formula (2).

8. The method according to claim 1, wherein
compound of formula (2) is prepared by a reduction of compound of formula (1).

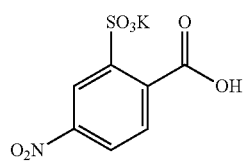
(1)

9. The method according to claim 8, wherein
the reduction is done with $H_2$, Fe, Zn, Sn, hydrazine or $NaBH_4$.

10. The method according to claim 8, wherein
the reduction is done with $H_2$.

11. The method according to claim 10, wherein
the reduction is done in the presence of a catalyst CAT, and CAT is Pd/C.

12. The method according to claim 10, wherein
the reduction is done in water as solvent.

13. The method according to claim 8, wherein
the reduction is done in the presence of small amounts of xylene, small amounts are molar amounts of from 0.01 to 2 eq of the molar amount of compound of formula (1).

* * * * *